United States Patent [19]

Johnson

[11] 4,129,093

[45] Dec. 12, 1978

[54] STAINING APPARATUS

[75] Inventor: Leighton C. Johnson, Edwardsburg, Mich.

[73] Assignee: Miles Laboratories, Inc., Elkhart, Ind.

[21] Appl. No.: 840,651

[22] Filed: Oct. 11, 1977

[51] Int. Cl.² ............................................ B05C 13/02
[52] U.S. Cl. .................................. 118/401; 118/503; 269/43; 269/296
[58] Field of Search ...................... 118/401, 503, 416; 211/41, 495; 269/43, 296

[56] References Cited

U.S. PATENT DOCUMENTS

| | | | |
|---|---|---|---|
| 1,721,503 | 7/1929 | Priess | 118/503 X |
| 2,522,416 | 9/1950 | Weiskopf | 118/503 |
| 2,817,313 | 12/1957 | Isreeli | 118/503 |
| 2,946,453 | 7/1960 | Pityo | 211/41 R |
| 2,953,253 | 9/1960 | Henderson et al. | 211/41 R |
| 4,066,250 | 1/1978 | Campbell | 269/43 |

*Primary Examiner*—John McIntosh
*Attorney, Agent, or Firm*—Roger N. Coe

[57] ABSTRACT

Apparatus is disclosed for applying liquid to a series of individual, substantially flat objects. The apparatus is particularly adapted for staining microscope slides. The apparatus comprises a fixed plate member and preferably an opposing plate member positioned substantially parallel to and movable toward and away from the fixed plate member, aligned by means of at least one guide member which engages said plate members. A series of movable spacing shims extend along the guide member for separating flat objects, such as glass slides. The flat objects are inserted into the apparartus while the movable plate member is positioned away from the fixed plate member. Once the flat objects have been inserted in the apparatus between adjacent spacing shims the movable plate member is moved toward the fixed plate member to clamp the flat objects in predetermined spaced parallel face-to-face relation. At least one opening located in the fixed plate member allows liquid to flow over adjacent edge portions of the flat objects and fill the capillary gaps formed between adjacent flat objects by the spacing shims.

13 Claims, 7 Drawing Figures

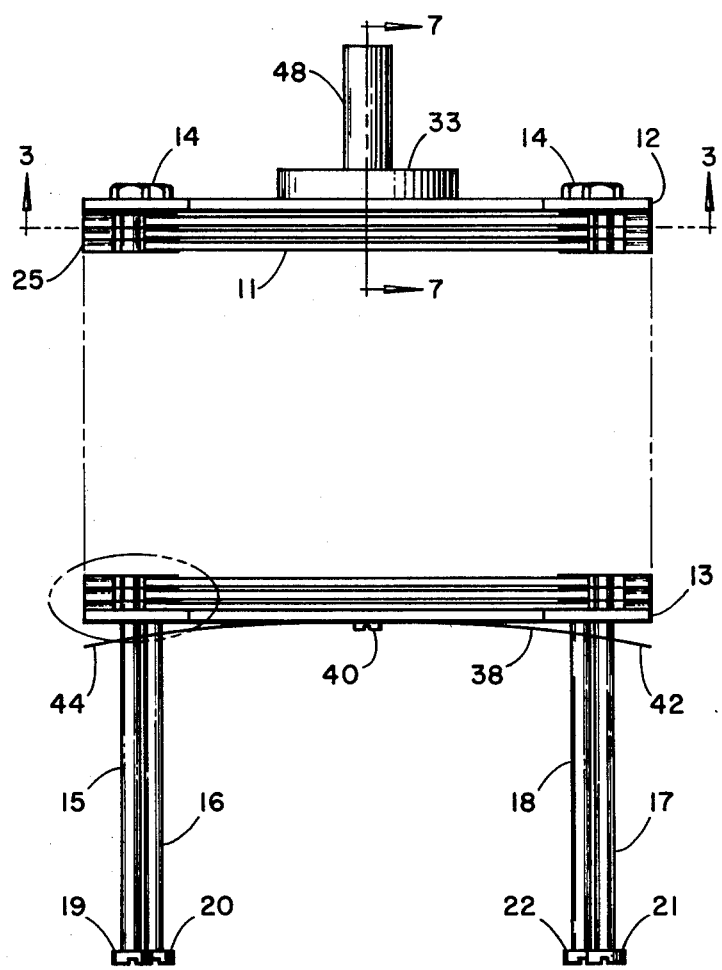
FIG. 5
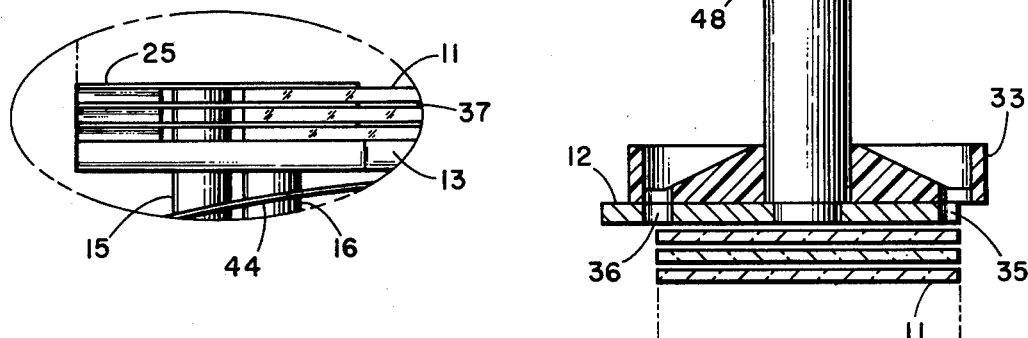
FIG. 6
FIG. 7

STAINING APPARATUS

FIELD OF THE INVENTION

The present invention relates to staining apparatus and, more particularly, to a collapsible staining rack for staining a multiplicity of microscope slides.

BACKGROUND OF THE INVENTION

In the biomedical field there are a number of procedures which involve treating specimens on microscope slides with various reagents. For example, in the fields of hematology, histology, cytology, microbiology and immunology various cultures, smears and organisms are placed on microscope slides and then treated with stains, counterstains, decolorizers, fixers, dehydrators, antigens, antibodies and washes to properly identify or differentiate the specimen under study.

Where these procedures are performed manually the various reagents are generally poured onto the slides and washed off, or the slides may be placed in racks and sequentially dipped in one reagent container after another. Each reagent is held in contact with a specimen a predetermined length of time and the racks are often placed in a rinse solution between treatment with the various reagents or dyes.

Dyes are normally very potent and messy to handle. Accordingly, dipping procedures, while simple, are lengthy and tedious considering the number of slides that may have to be prepared and the quality of the finished product can be affected by the procedure used, especially the freshness of a treatment solution.

Various devices have been proposed to mechanize or automate slide staining techniques. A very common approach is to provide an indexical slide rack which moves slides along a predetermined path dipping the slides into one container after another. Machines have also been constructed to transport individual slides along a processing platen where each slide is treated with various dyes and intermittent rinses. Another known device simply floods a slide chamber with dye and then causes the dye to be removed from the chamber before a new solution is introduced. These known devices generally are relatively large in dimension, and in many cases must discharge substantial amount of dye after only one cycle of use. In addition to other disadvantages, these devices and techniques can result in chemical and cellular cross contamination and interreaction with specimens on different slides unless care is taken in supplying and removing treating solution from the slides.

SUMMARY OF THE INVENTION

An object of the invention is to provide an improved system for staining microscope slides.

Another object of the present invention is to provide a system for reducing the amount of stain required to stain a slide.

Still another object of the present invention is to provide a system for staining slides which will substantially eliminate cross contamination problems during staining.

A further object of the present invention is to provide a system which can be readily adapted for uniformly staining a large and variable number of slides.

Yet another object of the present invention is to provide a convenient and economical system for staining microscope slides.

A still further object of the invention is to provide slide staining apparatus which is compact and easy to use.

The apparatus of the present invention for receiving a plurality of sudstantially flat objects and for positioning such objects in predetermined spaced parallel relationship is characterized by at least one guide member and spacer means movably connected to said at least one guide member, said spacer means being movable away from each other to a first position in which individual objects can be interposed between adjacent spacer means, said spacer means also being movable toward each other to a second position in which objects interposed therebetween are positioned thereby in predetermined spaced parallel relationship.

In accordance with a preferred embodiment of the present invention a collapsible staining rack is formed having opposing, substantially parallel fixed and moveable plate members aligned by means of at least one guide member which engages said plate members. A series of movable spacing shims supported by the guide member means separate the plate members. These movable shims are adapted to receive and separate flat objects, such as glass slides. Once the flat objects have been positioned in the staining rack substantially parallel to each other the collapsible rack is compressed by moving the movable plate member toward the fixed plate member. When compressed, the flat objects are spaced apart by the spacing shims with the thickness of the shims forming a capillary gap between adjacent flat objects.

To use the staining rack liquid is poured over the top edge of the rack causing the capillary gaps or spaces to sequentially fill until finally excess liquid drips from the bottom flat object, indicating that all capillary spaces are filled. Since there is no flow continuity over a specimen area of a flat object, no cellular cross contamination occurs. Excess liquid can be removed by spinning the collapsible staining rack.

BRIEF DESCRIPTION OF THE DRAWINGS

Other end further objects, advantages and features of the invention will be apparent to those skilled in the art from the following detailed description thereof, taken in conjunction with the accompanying drawings, in which:

FIG. 5 is a front view, partially shown in phantom outline, of the apparatus illustrated in FIG. 4;

FIG. 6 is an enlarged view of the portion in FIG. 5 illustrated by dashed elliptical outline; and FIG. 7 is a cross sectional view taken along lines 7—7 in FIG. 5.

DESCRIPTION OF THE PREFERRED EMBODIMENTS

The preferred apparatus forming the subject matter of the present invention is characterized by a fixed plate member; an opposing and substantially parallel movable plate member; at least two guide means interconnecting said fixed and movable plate members; a series of spacing shims attached to each of the guide means and positioned between said fixed and movable plate members adapted to receive and separate a series of substantially flat objects, maintaining the substantially flat objects parallel to each other and to the fixed and movable plate members, the apparatus being expansible to facilitate the insertion of substantially flat objects and compressible for use. When compressed the substantially flat objects are maintained apart from each other by a capillary gap, the thickness of which is identical to the thickness of a spacing shim.

Figure 1:
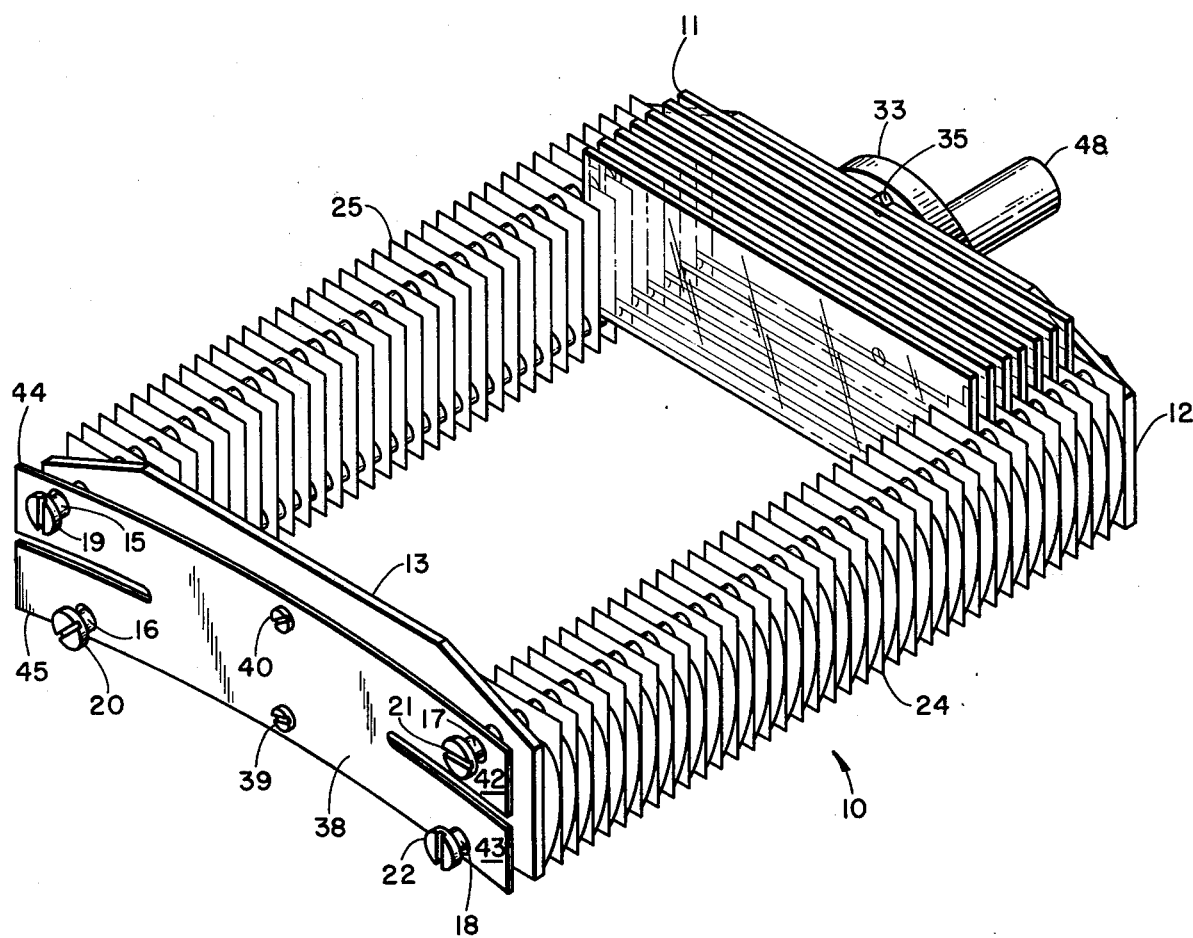
FIG. 1 is a perspective view showing apparatus of the present invention in an expanded position containing a few glass slides positioned therein.

Turning now to FIG. 1 of the drawings, collapsible slide rack 10 in accordance with the present invention is shown in expanded position for the insertion of glass slides, such as glass slides 11-11. Collapsible slide rack 10 is composed of a substantially rectangular fixed plate member 12 and an opposing parallel substantially rectangular movable plate member 13, which plate members are maintained in the same vertical plane by guide members 15, 16, 17, and 18. Rod like guide members 15, 16, 17, and 18, which extend perpendicular to plate members 12 and 13, are secured to fixed plate member 12 (by suitable means, such as nuts 14—14 shown in FIG. 4) and pass through openings in movable plate member 13. Enlarged ends 19, 20, 21, and 22 of rod like guide members 15-18, respectively, prevent movable plate member 13 from becoming disconnected from the guide members.

Figure 2:
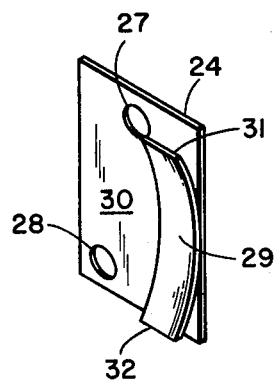
FIG. 2 is a perspective view showing one embodiment of a spacing shim which can be used in the apparatus of the present invention.

Spacing shims 24—24 and 25—25 are interconnected with guide members 17 and 18 and 15 and 16, respectively, and are positioned along said guide members between fixed plate member 12 and movable plate member 13 as shown in FIG. 1. As seen in FIG. 2 the spacing shims have a base 30 which is substantially rectangular in configuration. Two non-aligned openings 27 and 28 are present in the base of spacing shims 24 and positioned such that two guide members can pass through the openings. In addition, each spacing shim has a crescent shaped spring element 29 which is attached to rectangular base plate 30, as shown. Thus, when multiple spacing shims 24—24 are positioned as in FIG. 1 with guide members 17 and 18 passing through openings 27 and 28, respectively, curved ends 31 and 32 of crescent shaped spring element 29 which extend away from base 30 cause spacing shims 24—24 to expand in accordian fashion a distance sufficient to insert a flat object, such as glass slide 11, between base plates 30—30 of two adjacent spacing shims 24—24. The tension of crescent shaped spring element 29, however, is sufficiently weak to permit compression of curved ends 31 and 32 when movable plate member 13 is moved along guide members 15-18 toward fixed plate member 12. It will be understood that spacing shims 25 are mirror images of spacing shims 24.

Spring member 38 (FIGS. 1 and 5) extends along movable plate member 13 and is suitably attached to plate member 13, e.g., by means of two screws 39 and 40 centrally located in spring member 38. Spring member 38 has bifurcated end members which curve away from movable plate member 13, each of which has an opening for one of the guide members 15-18. Thus, end member 42 has an opening for guide member 17; end member 43 has an opening for guide member 18; end member 44 has an opening for guide member 15; and end member 45 has an opening for guide member 16. These openings for the guide members are such that when the bifurcated end members are pressed away from movable plate member 13 movable plate member 13 can be freely moved along guide members 15-18 and when the bifurcated end members are pressed toward movable plate member 13 binding occurs against the guide members so as to prevent free movement of movable plate member 13. Thus, spring member 38 allows collapsible slide rack 10 to be extended as illustrated in FIG. 1 for insertion or removal of slides and compressed as illustrated in FIG. 4 for staining.

Figure 3:
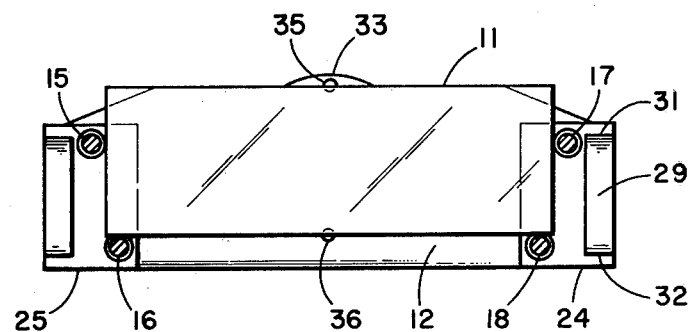
FIG. 3 is a sectional view taken along lines 3—3 in FIG. 5 and showing a glass slide resting on opposing spacing shims against the fixed plate member.

FIG. 3 illustrates a glass slide 11 resting on opposing spacing shims 24 and 25 against fixed plate member 12. The spacing of guide members 15 and 17 is slightly longer than the length of glass slide 11. Guide members 16 and 18, however, are spaced closer together and limit how far slide 11 can be inserted into slide rack 10. This arrangement facilitates the insertion and removal of slides in slide rack 10 and the alignment of the slides in the slide rack. When compressed to the position illustrated in FIG. 4 the slides are held so tightly as to be incapable of movement.

Figure 4:
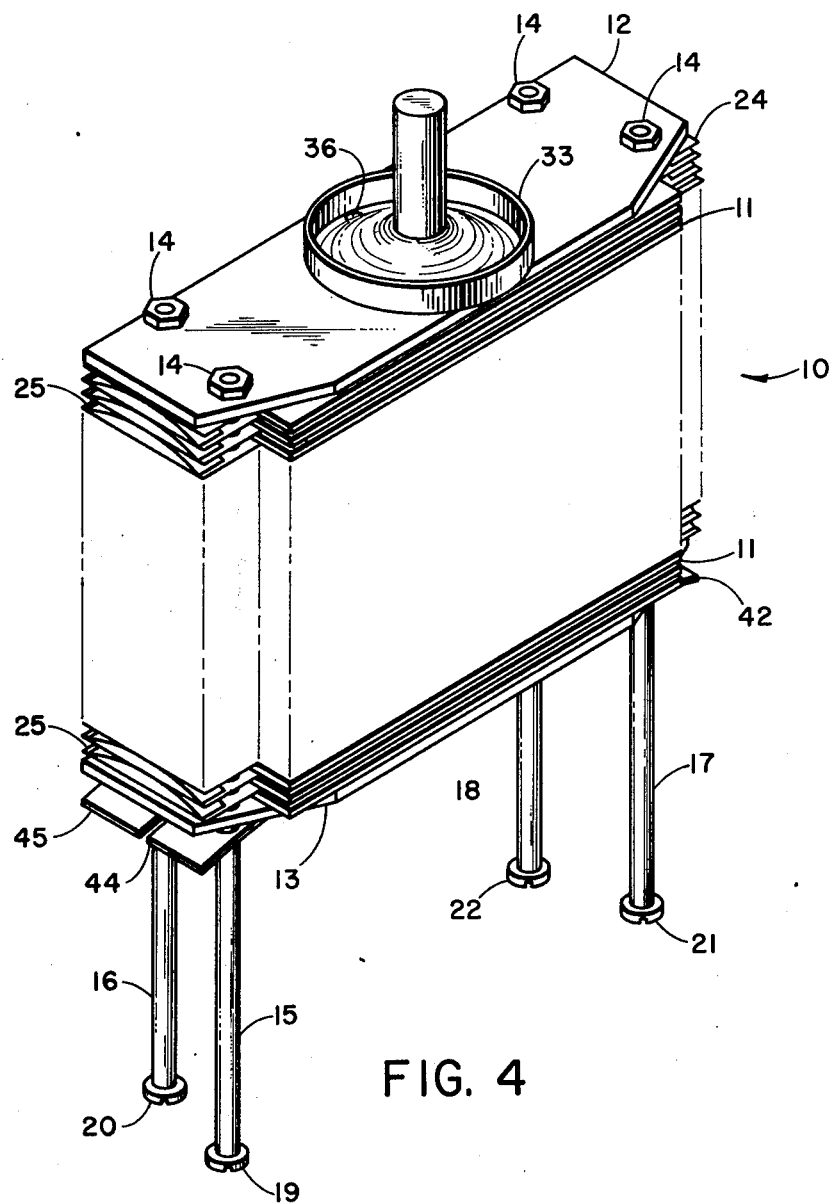
FIG. 4 is a perspective view, partially shown in phantom outline, of apparatus of the present invention in compressed position.

A portion of circular filling cup 33, attached to the top of fixed plate member 12, can also be seen in FIG. 4. Filling cup 33 has two holes 35 and 36 located on its outer perimeter (FIG. 7) and has a cone shaped center portion which channels liquids inside the cup downward through holes 35 and 36 and along the longitudinal edges of glass slides 11—11. The introduction of liquid through filling cup 33 occurs after compressing slides 11—11 (as shown in FIG. 4) by moving adjustable plate member 13 toward fixed plate member 12. In the compressed configuration slides 11—11 are separated from each other by the thickness of the spacing shims thereby creating a capillary gap 37—37 (FIG. 6) between slides. Liquid in filling cup 33 moves through holes 35 and 36 onto the two longitudinal edges of the first glass slide and into the capillary gap separating the first glass slide from the second glass slide. Once that capillary gap is filled excess liquid passes to the capillary gap separating the next two slides and so on until all of the capillary gaps are filled and excess liquid drips from the edge of the bottom slide.

Rod like pin 48 (as shown in FIGS. 1, 4 and 5) is connected to fixed plate member 12 in such a manner as to extend perpendicularly upward from the center of the mass of the assembly through filling cup 33 (see FIG. 7). Pin 48 provides a means for connecting collapsible slide rack 10 to means (not shown) for rotating the slide rack in order to remove excess liquid from slides 11—11. Thus, at the end of a predetermined interval of time or after a suitable sensor indicates that all capillary spaces between the slides are full, the staining rack can be rotated by apparatus (not shown) to remove excess liquid by spinning. The axis of rotation can be in a vertical direction or at a suitable angle. Spinning is especially valuable in procedures requiring a wash and removal step to separate bound (reacted) from unbound (unreacted) reagent, marker, antibody and the like.

If the slide staining rack has capacity for 50 slides, the staining rack can be used to stain any number of slides up to 50. If the number of slides present in the slide staining rack is substantially less than 50 it may be desirable to insert a filler block (not shown) into the rack to act as a spacer for missing slides. A filler block can be made of any suitable material, such as plastic, and can be formed so as to interconnect with other filler blocks in order to make a spacer of any desired thickness.

The spacing can also be adjusted by constructing the spacing shims in a manner such that they are attached to the staining rack by a frictional fit permitting them to be removed by simply pulling spacing shims from the rack. This makes it possible to readily adjust the number of spaces in the rack with the number of slides which are to be processed and also eliminates any necessity for inserting a filler block into the staining rack.

Each cresent shaped element can be formed either as an independant member connected by suitable means, such as spot welding to the base of the spacing shim, or can be made by cutting and shaping one side of the spacing shim base. Alternatively, other means, such as coil springs, can be attached to flat base members for the purpose of making a compressible shim.

Rather than being attached to opposite ends of the top member of the slide rack, the guide member(s) can be constructed to form an inverted "L" shaped configuration in conjunction with the top member. The guide member(s) in such an arrangement can be constructed to have movable dividing members capable of retaining slides with a capillary spacing when the slides are compressed by moving the slides toward the top member. In such an embodiment it is not necessary to have a moveable plate member.

Yet another alternative form of guide member is the telescoping guide member in which elements of a guide member nest in one another to permit extension or compression of the guide member, as desired.

The system of the present invention can be used with respect to a wide variety of staining procedures. For example, one specific staining procedure is known as the Gram-staining technique. This technique uses four reagents, crystal violet (blue), Gram's iodine (fixer), alcohol (decolorizer) and safranine (red).

In addition, the slide rack has utility for blood film staining (Wright stain), hematoxylin-eosin staining of tissue sections and in the Papnicolaou staining technique in exfoliative gynecological smear preparations. Furthermore, most immunohistochemical procedures, including the use of fluorescent and enzyme markers, lend themselves advantageously to the apparatus. The same is true of staining and destaining electrophoretic and isoelectric focusing plates in blood serum studies.

From the foregoing, it will be seen that this invention is well adapted to attain all of the ends and objects hereinabove set forth, together with other advantages which are obvious and which are inherent to the system. The new and improved slide staining apparatus requires no movement of the slides while stain is being applied. Cross contamination problems are essentially eliminated. Since no flow through occurs when the capillary gaps are filled, the apparatus of the present invention can even be used in a sequential dipping procedure provided excess treating liquid is removed between treatment containers. Cross contamination problems inherent with conventional dipping racks are obviated by this invention since the capillary gap for each flat object can be considered a separate chamber with no through flow, thus effectively isolating one specimen from another. The gap size can be adjusted as desired. In the preferred method of operation only a small volume of stain is required per slide. For example, at least 2,000 1 × 3 inch slides separated by a 0.008 inch capillary gap can be treated per liter of stain. This means that it is economical to use stain once and then discard the stain. Thus, the necessity for reclaiming used stain and the problems attendant to such reclamation are avoided. Contamination problems associated with the use of old stain are accordingly avoided. The system is versatile and various stains and staining methods can be utilized. Any number of slides can effectively be used since the system does not require that a full compliment of slides be present during each staining operation. In addition, the system avoids the necessity of using pumps and valves for supplying stain to the slides, thereby reducing cost as well as maintenance problems.

Obviously, the apparatus of the present invention does not require modification for utilization with slides which vary in thickness. Moreover, the nature of the apparatus is such that precise uniformity of width and length of a slide are not critical. By making appropriate modifications apparatus can be constructed to fit conventional one by three inch slides or adapted to hold other slides, such as two by three inch slides. In addition, the apparatus can be easily modified for holding cover slips or any other glass, plastic, or similar material which is to be treated with a liquid.

While emphasis has been placed on the use of a system for staining biological specimens, it will be understood, as previously indicated, that the concept has potential application in other areas, such as histochemistry, antinuclear antibody staining, tissue compatibility, etc. The invention also has applicability to such areas as photographic processing laboratories to reduce print and film or plate processing times by reducing manipulation or handling steps.

The material used for construction of the apparatus is not critical. Preferably, metal parts are non-corrosive, easily cleaned, light in weight, wear resistant, etc. Stainless steel has been found to be a suitable metal for such construction. The filling cup should be made from a material which is noncorrosive, inert to the stain used, readily cleanable, etc. A plastic, such as polyethylene, is a preferred material.

Obviously, many other modifications and variations of the invention as hereinabove set forth can be made without departing from the spirit and scope thereof.

What is claimed is:

1. Apparatus for holding a plurality of individual substantially flat objects parallel to each other and separated from each other by a capillary gap, which apparatus comprises:
   a top plate member having at least one opening adapted for the introduction of liquid along at least one edge of said substantially flat objects;
   a movable bottom plate member;
   at least one guide member interconnecting said top plate member with said bottom plate member; and
   a series of spacing shims adapted to at least one guide member between said top plate member and said bottom plate member, said shims being adapted to divide a series of individual substantially flat objects and maintain said substantially flat objects in an aligned position parallel to the top and bottom plate members such that the substantially flat objects are kept apart from each other by a capillary gap, the thickness of which is identical to the thickness of one of the shims.

2. The apparatus of claim 1 which further contains a bifurcated spring member attached to said bottom plate member, said bifurcated spring member being associated with said guide member in a fashion permitting the regulation of movement and position of said bottom plate.

3. The apparatus of claim 1 which further contains a reservoir chamber for liquid positioned on said top plate member, said reservoir chamber being adapted for introduction of liquid along at least one edge of said substantially flat objects.

4. The apparatus of claim 1 which further contains a pin attached to and extending from said top plate member, said pin being centrally disposed with respect to said top plate member and adapted for interconnection with means for rotating said apparatus.

5. The apparatus of claim 1 in which the substantially flat objects are microscope slides.

6. Apparatus for holding a plurality of individual substantially flat objects parallel to each other and separated from each other by a capillary gap, which apparatus comprises:
   a top plate member;
   a movable bottom plate member;
   at least one guide member interconnecting said top plate member with said bottom plate member; and
   a series of compressible spring elements acting as spacing shims attached to at least one guide member between said top plate member and said bottom plate member, said compressible spring elements being adapted to divide a series of individual substantially flat objects and maintain said substantially flat objects in an aligned position parallel to the top and bottom plate members such that the substantially flat objects are kept apart from each other by a capillary gap, the thickness of which is identical to the thickness of one of the compressible spring elements.

7. The apparatus of claim 6 in which each compressible spring element is mounted on a base member, which base member is attached to at least one guide member.

8. The apparatus of claim 6 in which said top plate member has at least one opening adapted for the introduction of liquid along at least one edge of said substantially flat objects.

9. The apparatus of claim 6 which further contains a bifurcated spring member attached to said bottom plate member, said bifurcated spring member being associated with said guide member in a fashion permitting regulation of movement and position of said bottom plate.

10. The apparatus of claim 6 which further contains a reservoir chamber for liquid positioned on said top plate member, said reservoir chamber having at least one opening adapted for introduction of liquid along at least one edge of said substantially flat objects.

11. The apparatus of claim 6 which further contains a pin attached to and extending from said top plate member, said pin being centrally disposed with respect to said top plate member and adapted for interconnection with means for rotating said apparatus.

12. The apparatus of claim 6 in which the substantially flat objects are microscope slides.

13. Apparatus for retaining a plurality of individual substantially flat objects parallel to each other and separated from each other by a capillary gap, which apparatus comprises:
   a top member;
   at least one guide member extending from said top member;
   separating means connected to said at least one guide member in a manner permitting movement of said separating means relative to said top member, each said separating means having compressible spring elements adapted for retaining a series of individual substantially flat objects parallel to each other and separating the flat objects by a capillary gap when the separating means are compressed against said top member; and
   compressing means for maintaining said separating means compressed against said top member.

* * * * *